United States Patent [19]

Rivier

[11] 4,288,335

[45] Sep. 8, 1981

[54] NOVEL METALLIC DITHIOPHOSPHATES AND THEIR USE AS ADDITIVES FOR LUBRICATING OILS

[75] Inventor: Georges Rivier, Bron, France

[73] Assignee: Orogil, Courbevoie, France

[21] Appl. No.: 127,049

[22] Filed: Mar. 4, 1980

[30] Foreign Application Priority Data

Mar. 9, 1979 [FR] France ............................. 79 06058

[51] Int. Cl.$^3$ ......................... C10M 1/48; C07F 3/06
[52] U.S. Cl. ......................... 252/32.7 E; 260/348.39; 546/6; 548/101
[58] Field of Search ............... 260/429.9, 429 R, 403, 260/348.39; 252/32.7 E; 546/6; 548/101

[56] References Cited

U.S. PATENT DOCUMENTS

| | | | |
|---|---|---|---|
| 2,177,983 | 10/1939 | Harris | 260/403 |
| 2,802,856 | 8/1957 | Norman et al. | 260/429.7 |
| 2,895,973 | 7/1959 | Ready et al. | 260/403 |
| 2,905,683 | 9/1959 | Goldsmith | 260/429.7 |
| 2,959,544 | 11/1960 | Smith et al. | 260/429.9 |
| 3,102,096 | 8/1963 | Nygaard et al. | 252/32.7 |
| 3,288,819 | 11/1966 | Tichelaar et al. | 260/399 |
| 3,944,495 | 3/1976 | Wiley et al. | 260/429.9 X |
| 4,044,032 | 8/1977 | Wiley et al. | 260/429 R |

FOREIGN PATENT DOCUMENTS

1310171 10/1962 France .

*Primary Examiner*—Helen M. S. Sneed
*Attorney, Agent, or Firm*—Herbert F. Schwartz; Ronald A. Schapira

[57] ABSTRACT

Metallic dithiophosphates of the formula:

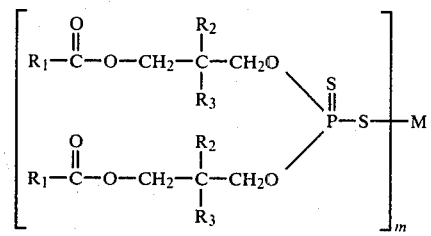

in which $R_1$ is an alkyl, alkenyl, cycloaliphatic, aryl, or heterocyclic radical, $R_2$ and $R_3$ are alkyl radicals, preferably $C_1$–$C_4$ radicals, and m represents the valence of the metal M, M being a metal of Groups IIB, IIIB, IVB, or VIII of the Periodic System of Elements, preferably zinc. They are obtained by the action of $P_2S_5$ on a monoester alcohol of the formula:

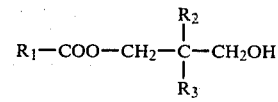

and then by reaction of a metal oxide, such as zinc oxide, with the dithiophosphoric acid formed. These metallic dithiophosphates are useful as extreme-pressure and anti-wear additives for lubricating oils in amounts of between 0.2 and 10 percent, referred to the weight of lubricating oils.

37 Claims, No Drawings

NOVEL METALLIC DITHIOPHOSPHATES AND THEIR USE AS ADDITIVES FOR LUBRICATING OILS

BACKGROUND OF THE INVENTION

The present invention relates to novel metallic dithiophosphates and their use as extreme-pressure and anti-wear additives for lubricating oils.

U.S. Pat. No. 3,944,495 discloses that automatic transmission fluids can be improved by the addition of metallic dithiophosphates of the formula:

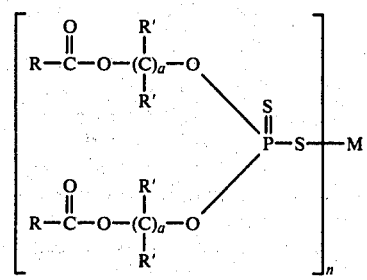

in which:

R represents a saturated $C_4$–$C_{30}$ aliphatic radical;

R' represents hydrogen, a $C_1$–$C_6$ alkyl radical, or a $C_6$–$C_9$ aryl radical;

a is a whole number between 2 and 12;

n corresponds to the valence of the metal M; and

M represents an alkaline or alkaline-earth metal or a transition metal.

Such products are particularly well adapted to use in automatic transmission fluids, which do not require additives of great thermal stability.

On the other hand, such products are not sufficiently thermally stable to be used as additives for crankcase oils and, in particular, for crankcase diesel oils.

It is also known that the properties of lubricating oils can be improved, as disclosed in French Pat. No. 1,310,171 (U.S. counterpart, U.S. Pat. No. 3,102,096), by using metallic dialkyldithiophosphates prepared from monoalcohols of the "neo" type, that is to say, alcohols in which the carbon atom adjacent the carbon atom fixed to the hydroxyl group is fully replaced by alkyl groups. Such products have the drawback that they are of only average effectiveness and, furthermore, cannot be used industrially, due to the high cost of the "neo" monoalcohols.

By the present invention, new thermally stable metallic dithiophosphates have been discovered which can be used industrially in order, in particular, to improve the extreme-pressure and anti-wear properties of lubricating oils.

It is an object of the present invention to provide novel metallic dithiophosphates which improve the extreme-pressure and anti-wear properties of lubricating oils and which overcome the disadvantages of the prior art.

It is another object of the present invention to provide a novel process for the preparation of the metallic dithiophosphate oil additives of the invention.

It is a further object of the invention to provide novel lubricating oil compositions containing the metallic dithiophosphate additives of the invention.

Other objects will be apparent to those skilled in the art from the present description.

GENERAL DESCRIPTION OF THE INVENTION

The novel metallic dithiophosphates of the invention comprise compounds of the formula:

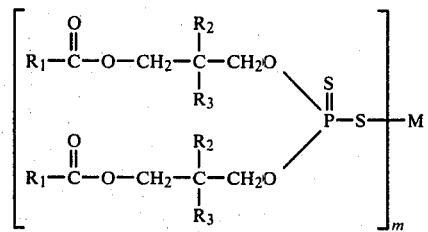

in which formula:

$R_1$ represents:

(1) a linear or branched alkyl radical containing from about 1 to 24 carbon atoms, and preferably, about 1 to 17 carbon atoms, optionally substituted by at least one phenyl, halo- or heterocyclic group containing 1 or more heteroelements, selected from among nitrogen, sulfur, and oxygen;

(2) a linear or branched alkenyl radical containing from about 2 to 24 carbon atoms, and preferably, about 2 to 17 carbon atoms, optionally substituted by at least one phenyl, halo- or heterocyclic group containing 1 or more heteroelements selected from among nitrogen, sulfur, or oxygen;

(3) a saturated or unsaturated cycloaliphatic or polycycloaliphatic radical containing from about 3 to 20 carbon atoms, optionally substituted by 1 or more alkyl groups containing from about 1 to 12 carbon atoms or halogen;

(4) an aryl radical containing from about 6 to 14 carbon atoms, and preferably, 6 carbon atoms, possibly substituted by 1 or more alkyl groups containing from about 1 to 12 carbon atoms or halogen or halo-alkyl;

(5) a heterocyclic radical containing one or more heteroelements selected from among nitrogen, sulfur and oxygen, optionally substituted by 1 or more alkyl groups containing from about 1 to 12 carbon atoms or halogen;

$R_2$ and $R_3$ are the same or different and represent an alkyl radical containing from about 1 to 12 carbon atoms, and preferably, from 1 to 4 carbon atoms;

m represents the valence of the metal M; and

M represents a metal from the groups IIB, IIIB, IVB, or VIII of the Periodic System of Elements and, in particular, zinc.

As examples of $R_1$ radicals there are the following: methyl, 1,2-dichloro ethyl, heptyl, 10-bromo decyl, 8,9-dibromo heptadecyl, heptadecyl, vinyl, phenylvinylene, 2-furyl vinylene, isopropenyl, decenyl, heptadecenyl, cyclopropyl, cyclohexyl, cyclohexenyl, $C_{19}H_{29}$ radicals derived from abietic acid, phenyl, p-chlorophenyl, p-trifluoromethylphenyl, 2,3-dimethyl-1-phenyl, p-octylphenyl, 2-furyl, 4-methyl-5-thiazolyl, and 3-pyridyl.

As examples of $R_2$ or $R_3$ radicals are the methyl ethyl, and n-butyl radicals.

The new products forming the object of the invention can be prepared by the action of a basic compound of the metal M, and in particular by action of zinc oxide, where the metal is zinc, on a dithiophosphoric acid of formula (I), below:

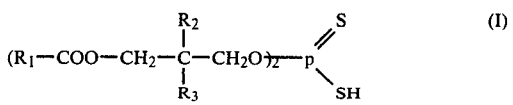

in which $R_1$, $R_2$ and $R_3$ have the meaning given above, with an amount of basic compound of metal M between the amount stoichiometrically necessary to neutralize the said dithiophosphoric acid and twice said stoichiometric amount.

This operation can be carried out at a temperature of between about 20° and 200° C., and preferably between about 60° C. and 150° C., with an amount of basic compound of metal M of preferably between about 1.1 and 1.5 times the stoichiometric amount.

The dithiophosphoric acid of formula (I) can be prepared by action of phosphorus pentasulfide on a monoester alcohol of formula (II), below:

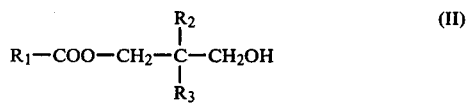

in which $R_1$, $R_2$ and $R_3$ have the meaning indicated above, with an amount of $P_2S_5$ corresponding preferably to about a 5 to 20 molar percent excess of $P_2S_5$ over the stoichiometric quantity.

This operation can be carried out at a temperature of between about 50° and 200° C., and preferably between about 70° and 150° C., with a quantity of $P_2S_5$ corresponding preferably to a 5 percent molar excess over the stoichiometric quantity.

The monoester alcohol of formula (II) can be prepared by action of an acid of formula $R_1COOH$, in which $R_1$ has the meaning indicated above, with a diol of formula (III), below:

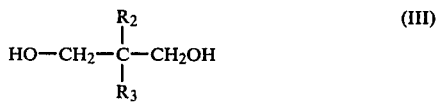

in which $R_2$ and $R_3$ have the meaning given above, with a molar ratio of acid to diol of between about 1:1 and 1:15 and, preferably, between about 1:2 and 1:12. This operation can be carried out at a temperature of between about 50° and 300° C., and preferably between about 80° and 200° C. in the presence of an acid catalyst.

Among the acids of formula $R_1COOH$ which can be employed are: acetic acid, 2,3-dichloro-propanoic acid, octanoic acid, 11-bromo-undecanoic acid, 9,10-dibromo-octadecanoic acid, stearic acid, acrylic acid, cinnamic acid, 2-furanacrylic acid, methacrylic acid, undecylenic acid, oleic acid, cyclopropane carboxylic acid, cyclohexane carboxylic acid, 1-cyclohexane carboxylic acid, abietic acid, benzoic acid, p-chlorobenzoic acid, p-trifluoromethylbenzoic acid, 2,3-dimethylbenzoic acid, p-n-octyl benzoic acid, 2-furan-carboxylic acid, 4-methyl-5-thiazol carboxylic acid, and nicotinic acid.

Among the diols of formula (III) which can be used are neopentylglycol and 2-ethyl-2-n-butyl-1,3-propanediol.

The present invention includes among its important objects the use of the metallic dithiophosphates of the invention as extreme-pressure and anti-wear additives for lubricating oils. Among the lubricating oils which can be improved by the addition of the said metallic dithiophosphates are the natural oils of a viscosity of between about 20.6 cst (centistokes) and 541 cst at 37.8° C. (namely, between 100 and 2500 SUS (Saybolt Universal Viscosity) at 100° F.), or of the synthetic or semi-synthetic oils (synthetic hydrocarbons, esters, polyesters, polyethers) of comparable viscosities.

The amounts of the said metallic dithiophosphates which are desirably introduced into the lubricating oils are between about 0.2 and 10 percent by weight of the lubricating oils. Within this range, the preferred amounts of metallic dithiophosphates employed are a function of the future use of the oil, namely, as crankcase oil, automatic transmission oil, hydraulic fluid, or cutting oil for the machine industry.

Anti-oxidant, anti-corrosion, anti-foam, and detergent-dispersant additives, other extreme-pressure and anti-foam additives, etc., can be introduced without any problem with regard to compatibility or loss of level of performance.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Preparation of zinc-bis-0,0-(2,2-dimethyl-1,3-propanediylmonooleate)-dithiophosphate of the formula:

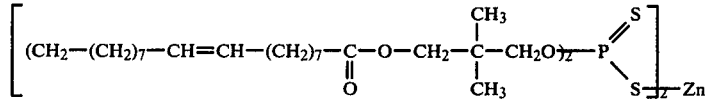

(a) Preparation of the monooleate of 2,2-dimethyl-1,3-propanediol

Into a 1-liter, three-neck round-bottom flask there were introduced:

282 g. (namely, 1 mol) of oleic acid;
416 g. (namely, 4 mols) of neopentylglycol (about 1 percent water); and
14 g. of acid earth having a base of hydrochloric acid (CLARCIL earth marketed by Sud-Chemie AG).

Heating of the mixture was effected at 180° C. for 4 hours while maintaining a pressure of 50 mm. Hg.; 24.5 g. of water distill off.

After cooling the remaining mixture, 300 g. of hexane and 100 g. of water were introduced. The mixture was agitated for 30 minutes, whereupon the organic layer was separated by settling. This washing operation was repeated three times. The organic phase collected was distilled to remove the solvent. In this way, there were recovered 356 g. (namely, 0.967 mol) of the desired ester, having a purity of 95.6 percent (determined by nuclear magnetic resonance), the remaining impurity being neopentylglycol. The yield of ester was 96.7 percent with respect to the oleic acid.

(b) Preparation of bis-0,0-(2,2-dimethyl-1,3-propanediyl-monooleate)-dithiophosphoric acid Into a 1-liter, three-neck round-bottom flask there were introduced 346.4 g. (namely, 0.9 mol) of the above prepared ester, and then, over the course of 3 hours, 50 g. (namely, 0.225 mol) of phosphorus pentasulfide, maintaining the temperature at 115° C. After the addition of the $P_2S_5$, the temperature was kept at 115° C. for 30 minutes, whereupon the traces of $H_2S$ resulting were eliminated by gradually decreasing the pressure to 30 mm. Hg. 380 g. of the desired dithiophosphoric acid were obtained having the following composition, as determined by elementary analysis:

|  | Calculated | Found |
|---|---|---|
| Phosphorus | 3.73% | 3.6% |
| sulfur | 7.71% | 7.2% |

(c) Neutralization by zinc oxide

Into a 1-liter, three-neck, round-bottom flask there were introduced the 380 g. (namely, 0.46 mol) of dithiophosphoric acid prepared above, whereupon there were added, in the course of 1 hour, 22.3 g. (namely, 0.276 mol) of zinc oxide (which represents a 30 percent excess over the stoichiometric amount), maintaining the temperature at 105° C. After the addition of the zinc oxide, the pressure was gradually decreased to 30 mm. Hg. to eliminate the water of formation. After cooling, the medium was taken up by 500 ml. of hexane and then filtered in order to eliminate the excess zinc oxide.

In this way, there were obtained 315 g. of the desired zinc dithiophosphate, which was a viscous, clear, slightly colored compound having a pH of 5.2.

The composition of the product obtained, determined by elementary analysis, was as follows:

|  | Calculated | Found |
|---|---|---|
| Phosphorus | 3.60% | 3.7% |
| Zinc | 3.78% | 3.5% |
| Sulfur | 7.43% | 7.2% |

EXAMPLE 2

Preparation of zinc-bis-0,0-(2,2-dimethyl-1,3-propanediylmonooctanoate)-dithiophosphate of the formula:

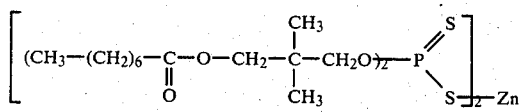

(a) Preparation of the monooctanoate of 2,2-dimethyl-1-propanol

The operation described in Example 1, part (a), was repeated, starting with:

144 g. (namely, 1 mol) of octanoic acid;

416 g. (namely, 4 mols) of neopentylglycol; and
14 g. of CLARCIL
for 5 hours at 170° C.

188 g. of the desired ester are recovered in a yield of 80 percent and a purity of 98 percent.

(b) Preparation of bis-(2,2-dimethyl-1,3-propanediyl-monooctanoate)-dithiophosphoric acid The operation described in Example 1, part (b), was repeated, starting with:

117.5 g. (namely, 0.5 mol) of the above-prepared ester;

27.8 g. (namely, 0.125 mol) of $P_2S_5$.

There were obtained 132 g. of the desired dithiophosphoric acid, the composition of which, determined by elementary analysis, was as follows:

|  | Calculated | Found |
|---|---|---|
| Phosphorus | 5.60% | 5.5% |
| Sulfur | 11.55% | 11.2% |

(c) Neutralization by zinc oxide

The operation described in Example 1, part (c), was repeated, starting with:

111 g. (namely, 0.2 mol) of the above-prepared dithiophosphoric acid;

10.5 g. (namely, 0.13 mol) of ZnO (30 percent excess).

In this way, there were obtained 105 g. of the desired zinc dithiophosphate of a pH of 5.5, having the following composition:

|  | Calculated | Found |
|---|---|---|
| Phosphorus | 5.29% | 5.1% |
| Zinc | 5.55% | 5.0% |
| Sulfur | 10.93% | 10.8% |

EXAMPLE 3

Preparation of zinc-bis-0,0-(2,2-dimethyl-1,3-propanediylmonoacrylate)-dithiophosphate of the formula:

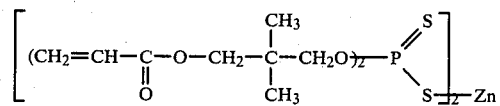

(a) Preparation of 2,2-dimethyl-1-propanol monoacrylate

The operation described in Example 1, part (a), was repeated, starting with:

72 g. (namely, 1 mol) of acrylic acid;
416 g. (namely, 4 mols) of neopentylglycol; and
14 g. of CLARCIL
for 10 hours at 150° C.

98 g. of the desired ester were recovered in a yield of 52 percent and a purity of 84 percent.

(b) Preparation of bis-0,0-(2,2-dimethyl-1,3-propanediyl-monoacrylate)-dithiophosphoric acid The operation described in Example 1, part (b), was repeated, starting with:

91.6 g. (namely, 0.5 mol) of the above-prepared ester; and 27.8 g (namely, 0.125 mol) of $P_2S_5$.

97 g. of the desired dithiophosphoric acid were obtained, having the following composition as determined by elementary analysis:

|  | Calculated | Found |
|---|---|---|
| Phosphorus | 7.56% | 7.3% |
| Sulfur | 15.61% | 15% |

(c) Neutralization by zinc oxide

The operation described in Example 1, part (c), was repeated, starting with:

82 g. (namely, 0.2 mol) of the above-prepared dithiophosphoric acid; and 10.5 g. (namely, 0.13 mol) of ZnO.

84 g. of the desired zinc dithiophosphate were obtained having a pH of 4.9 and the following composition:

|  | Calculated | Found |
|---|---|---|
| Phosphorus | 7.02% | 6.9% |
| Zinc | 7.36% | 7.2% |
| Sulfur | 14.50% | 13.9% |

EXAMPLE 4

Preparation of zinc-bis-0,0-[2,2-dimethyl-1,3-propanediylmono(cyclopropane carboxylate)]-dithiophosphate of the formula:

$$\left[ (CH_2 \underset{CH_2}{\overset{}{\diagdown}} CH_2 - \underset{O}{\overset{}{\underset{\|}{C}}} - O - CH_2 - \underset{CH_3}{\overset{CH_3}{\underset{|}{C}}} - CH_2O)_2 - P \underset{S}{\overset{S}{\diagup}} \right]_{\frac{1}{2}} Zn$$

(a) Preparation of the mono(cyclopropane dicarboxylate) of 2,2-dimethyl-1-propanol The operation described in Example 1, part (a), was repeated, starting with:

86 g. (namely, 1 mol) of cyclopropane carboxylic acid;

416 g. (namely, 4 mols) of neopentylglycol; and 14 g. of CLARCIL for 4 hours at 100° C.

150 g. of the desired ester of a purity of 89 percent were recovered in a yield of 77.6 percent.

(b) Preparation of bis-0,0-[2,2-dimethyl-1,3-propanediyl-mono(cyclopropane carboxylate)]-dithiophosphoric acid The operation described in Example 1, part (b), was repeated, starting with:

95.5 g. (namely, 0.5 mol) of the above-prepared ester;

27.8 g. (namely, 0.125 mol) of P₂S₅.

105 g. of the desired dithiophosphoric acid were obtained, having the following composition:

|  | Calculated | Found |
|---|---|---|
| Phosphorus | 7.08% | 6.9% |
| Sulfur | 14.61% | 14.4% |

(c) Neutralization by zinc oxide

The operation described in Example 1, part (c), was repeated, starting with:

87.5 g. (namely, 0.2 mol) of the above-prepared dithiophosphoric acid; and 10.5 g. (namely, 0.13 mol) of ZnO (30 percent excess).

In this way, there were obtained 90 g. of the desired zinc dithiophosphate of a pH of 5.1, having the following composition:

|  | Calculated | Found |
|---|---|---|
| Phosphorus | 6.61% | 6.5% |
| Sulfur | 13.66% | 13.4% |
| Zinc | 6.94% | 6.3% |

EXAMPLE 5

Preparation of zinc-bis-0,0-[2,2-dimethyl-1,3-propanediylmono(1-cyclohexene-carboxylate)]-dithiophosphate of the formula:

$$\left[ \underset{}{\bigcirc} - \underset{O}{\overset{}{\underset{\|}{C}}} - O - CH_2 - \underset{CH_3}{\overset{CH_3}{\underset{|}{C}}} - CH_2O)_2 - P \underset{S}{\overset{S}{\diagup}} \right]_{\frac{1}{2}} Zn$$

(a) Preparation of 2,2-dimethyl-1-propanol-mono(1-cyclohexene carboxylate)

The operation described in Example 1, part (a), was repeated, starting with:

126 g. (namely, 1 mol) of 1-cyclohexene-1-carboxylic acid;

416 g. (namely, 4 mols) of neopentylglycol; and 14 g. of CLARCIL for 6 hours at 160° C.

199 g. of the desired ester were recovered in a yield of 85.5 percent and a purity of 91 percent.

(b) Preparation of bis-0,0-[2,2-dimethyl-1,3-propanediyl-mono(cyclohexene-carboxylate)]-dithiophosphoric acid The operation described in Example 1, part (b), was repeated, starting with:

84.8 g. (namely, 0.4 mol) of the above-prepared ester;

22.2 g. (namely, 0.1 mol) of P₂S₅.

98 g. of the desired dithiophosphoric acid were obtained having the following composition:

|  | Calculated | Found |
|---|---|---|
| Phosphorus | 5.98% | 5.7% |
| Sulfur | 12.37% | 12.0% |

(c) Neutralization by zinc oxide

The operation described in Example 1, part (c), was repeated, starting with:

51.8 g. (namely, 0.1 mol) of the above-prepared dithiophosphoric acid; and 5.3 g. (namely, 0.065 mol) of ZnO (30 percent excess).

50 g. of the desired zinc dithiophosphate having a pH of 5.0 were thus obtained, with the following composition:

|  | Calculated | Found |
|---|---|---|
| Phosphorus | 5.64% | 5.3% |
| Zinc | 5.91% | 5.1% |
| Sulfur | 11.65% | 11.3% |

EXAMPLE 6

Preparation of zinc-bis-0,0-[2,2-dimethyl-1,3-propanediylmono(2-furan-carboxylate)]-dithiophosphate of the formula:

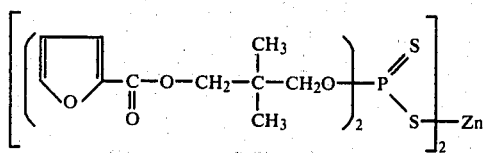

(a) Preparation of the mono(2-furan-carboxylate) of 2,2-dimethyl-1-propanol

The operation described in Example 1, part (a), was repeated, starting with:

112 g. (namely, 1 mol) of 2-furan-carboxylic acid;
416 g. (namely, 4 mols) of neopentylglycol; and
14 g. of CLARCIL for 7 hours at 170° C.

180 g. of the desired ester were recovered in a yield of 81.8 percent and a purity of 90 percent.

(b) Preparation of bis-0,0-[2,2-dimethyl-1,3-propanediyl-mono(2-furan-carboxylate)]-dithiophosphoric acid The operation described in Example 1, part (b), was repeated, starting with:

132 g. (namely, 0.6 mol) of the above-prepared ester; and
33.5 g. (namely, 0.15 mol) of $P_2S_5$.

140 g. of the desired dithiophosphoric acid were obtained, having the following composition:

|  | Calculated | Found |
|---|---|---|
| Phosphorus | 6.33% | 6.1% |
| Sulfur | 13.06% | 12.8% |

(c) Neutralization by zinc oxide

The operation described in Example 1, part (c), was repeated, starting with:

98 g. (namely, 0.2 mol) of the above-prepared dithiophosphoric acid; and
10.5 g. (namely, 0.13 mol) of ZnO (30 percent excess).

101 g. of the desired zinc dithiophosphate were obtained having a pH of 5.3 and the following composition:

|  | Calculated | Found |
|---|---|---|
| Phosphorus | 5.94% | 5.7% |
| Zinc | 6.23% | 6.0% |
| Sulfur | 12.27% | 11.9% |

EXAMPLE 7

Preparation of zinc-bis-0,0-[2,2-dimethyl-1,3-propanedyl-monoabietate]-dithiophosphate of the formula:

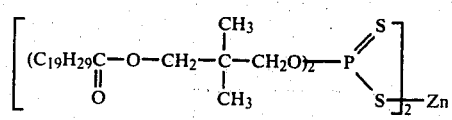

(a) Preparation of the monoabietate of 2,2-dimethyl-1-propanol

The operation described in Example 1, part (a), was repeated, starting with:

293 g. (namely, 1 mol) of abietic acid;
146 g. (namely, 4 mols) of neopentylglycol; and
14 g. of CLARCIL for 5 hours at 150° C.

280 g. of the desired ester were recovered with a yield of 70 percent and a purity of 95 percent.

(b) Preparation of bis-0,0(2,2-dimethyl-1,3-propanediyl-monoabietate)-dithiophosphoric acid The operation described in Example 1, part (b), was repeated, starting with:

240 g. (namely, 0.6 mol) of the above-prepared ester; and
33.5 g. (namely, 0.15 mol) of $P_2S_5$.

250 g. of the desired dithiophosphoric acid were obtained, having the following composition:

|  | Calculated | Found |
|---|---|---|
| Phosphorus | 3.64% | 3.5% |
| Sulfur | 7.51% | 7.5% |

(c) Neutralization by zinc oxide

The operation described in Example 1, part (c), was repeated, starting with:

170 g. (namely, 0.2 mol) of the above-prepared dithiophosphoric acid;
10.5 g. (namely, 0.13 mol) of ZnO (30 percent excess).

There are thus obtained 165 g. of the desired zinc dithiophosphate of a pH of 5.2, having the following composition:

|  | Calculated | Found |
|---|---|---|
| Phosphorus | 3.51% | 3.4% |
| Zinc | 3.68% | 3.4% |
| Sulfur | 7.24% | 7.0% |

EXAMPLE 8

Preparation of zinc-bis-0,0-[2,2-dimethyl-1,3-propanediyl-mono(2,3-dimethyl-benzoate)]-dithiophosphate of the formula:

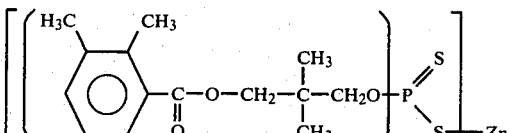

(a) Preparation of the mono(2,3-dimethyl-benzoate) of 2,2-dimethyl-1-propanol

The operation described in Example 1, part (a), was repeated, starting with:

150 g. (namely, 1 mol) of 2,3-dimethyl-benzoic acid;
416 g. (namely, 4 mols) of neopentylglycol; and
14 g. of CLARCIL for 5 hours at 150° C.

138 g. of the desired ester are recovered in a yield of 50 percent and a purity of 85 percent.

(b) Preparation of bis-0,0-[2,2-dimethyl-1,3-propanediyl-mono(2,3-dimethyl-benzoate)]-dithiophosphoric acid The operation described in Example 1, part (b), was repeated, starting with:

110 g. (namely, 0.4 mol) of the above-prepared ester; and 22.2 g. (namely, 0.1 mol) of P$_2$S$_5$.

103 g. of the desired dithiophosphoric acid were obtained, having the following composition:

|  | Calculated | Found |
|---|---|---|
| Phosphorus | 5.48% | 5.3% |
| Zinc | 11.31% | 11.1% |

(c) Neutralization by zinc oxide

The operation described in Example 1, part (c), was repeated, starting with:

84.9 g. (namely, 0.15 mol) of the above-prepared dithiophosphoric acid;

7.9 g. (namely, 0.0975 mol) of ZnO (30 percent excess).

There were thus obtained 85 g. of the desired zinc dithiophosphate of a pH of 5.3, having the following composition:

|  | Calculated | Found |
|---|---|---|
| Phosphorus | 5.19% | 5.1% |
| Zinc | 5.44% | 5.1% |
| Sulfur | 10.71% | 10.2% |

EXAMPLE 9

Preparation of zinc-bis-0,0-[2,2-dimethyl-1,3-propanediyl-mono(4-n-octyl-benzoate)]-dithiophosphate of the formula:

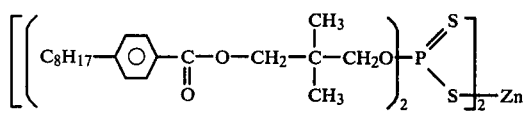

(a) Preparation of the mono(para-n-octyl-benzoate) of 2,2-dimethyl-1-propanol

The operation described in Example 1, part (a), was repeated, starting from:

234 g. (namely, 1 mol) of para-n-octyl-benzoic acid;
416 g. (namely, 4 mols) of neopentylglycol; and
14 g. of CLARCIL
for 7 hours at 170° C.

298 g. of the desired ester were recovered in a yield of 88 percent and a purity of 95 percent.

(b) Preparation of 0,0-[2,2-dimethyl-1,3-propanediyl-mono(4-n-octyl-benzoate)]-dithiophosphoric acid The operation described in Example 1, part (b), was repeated, starting with:

202 g. (namely, 0.6 mol) of the above-prepared ester; and 33.5 g. (namely, 0.15 mol) of P$_2$S$_5$.

201 g. of the desired dithiophosphoric acid were obtained having the following composition:

|  | Calculated | Found |
|---|---|---|
| Phosphorus | 4.41% | 4.3% |
| Sulfur | 9.10% | 9.0% |

(c) Neutralization by zinc oxide

The operation described in Example 1, part (c), was repeated, starting with:

140.6 g. (namely, 0.2 mol) of the above-prepared dithiophosphoric acid; and 10.5 g. (namely, 0.13 mol) of ZnO (30 percent excess).

138 g. of the desired zinc dithiophosphate were thus obtained having a pH of 5.4 and the following composition:

|  | Calculated | Found |
|---|---|---|
| Phosphorus | 4.22% | 4.1% |
| Zinc | 4.42% | 4.2% |
| Sulfur | 8.71% | 8.5% |

EXAMPLE 10

Preparation of zinc-bis-0,0-(2,2-dimethyl-1,3-propanediyl-monocinnamate)-dithiophosphate of the formula:

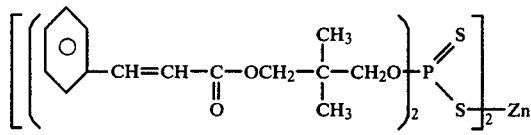

(a) Preparation of the monocinnamate of 2,2-dimethyl-1-propanol

The operation described in Example 1, part (a), was repeated, starting with:

148 g. (namely, 4 mols) of cinnamic acid;
416 g. (namely, 4 mols) of neopentylglycol; and
14 g. of CLARCIL
for 6 hours at 170° C.

158 g. of the desired ester of a purity of 89 percent are obtained in a yield of 60 percent.

(b) Preparation of bis-0,0-(2,2-dimethyl-1,3-propanediyl-monocinnamate)-dithiophosphoric acid The operation described in Example 1, part (b), was repeated, starting with:

132 g. (namely, 0.5 mol) of the above-prepared ester; and 27.8 g. (namely, 0.125 mol) of P$_2$S$_5$.

128 g. of the desired dithiophosphoric acid were obtained, having the following composition:

|  | Calculated | Found |
|---|---|---|
| Phosphorus | 5.52% | 5.4% |
| Sulfur | 11.39% | 11.2% |

(c) Neutralization by zinc oxide

The operation described in Example 1, part (c), was repeated, starting with:

112 g. (namely, 0.2 mol) of the above-prepared dithiophosphoric acid; and 10.5 g. (namely, 0.13 mol) of ZnO (30 percent excess).

105 g. of the desired zinc dithiophosphate of a pH of 5.4 and of the following composition were thus obtained:

|  | Calculated | Found |
|---|---|---|
| Phosphorus | 5.22% | 5.2% |
| Zinc | 5.48% | 5.2% |
| Sulfur | 10.78% | 10.5% |

EXAMPLE 11

Preparation of zinc-bis-0,0-(2,2-dimethyl-1,3-propanediyl)-2-monofuranacrylate)-dithiophosphate of the formula:

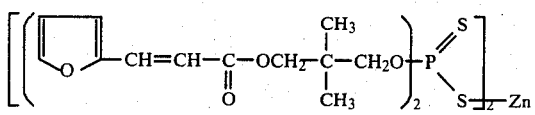

(a) Preparation of 2,2-dimethyl-1-propanol-2-monofuranacrylate

The operation described in Example 1, part (a), was repeated, starting with:

138 g. (namely, 1 mol) of 2-furanacrylic acid;
416 g. (namely, 4 mols) of neopentylglycol; and
14 g. of CLARCIL for 7 hours at 160° C.

102 g. of the desired ester are recovered in a yield of 40 percent and a purity of 88 percent.

(b) Preparation of bis-0,0-(2,2-dimethyl-1,3-propanediyl-2-monofuranacrylate)-dithiophosphoric acid The operation described in Example 1, part (b), was repeated, starting with:

77 g. (namely, 0.3 mol) of the above-prepared ester; and
16.7 g. (namely, 0.075 mol) of $P_2S_5$.

72 g. of the desired dithiophosphoric acid having the following composition were obtained:

|  | Calculated | Found |
|---|---|---|
| Phosphorus | 5.72% | 5.65% |
| Sulfur | 11.81% | 11.7% |

(c) Neutralization by zinc oxide

The operation described in Example 1, part (c), was repeated, starting with:

54 g. (namely, 0.1 mol) of the above-prepared dithiophosphoric acid; and
5.3 g. (namely, 0.065 mol) of ZnO (30 percent excess).

50 g. of the desired zinc dithiophosphate of a pH of 3.7 and the following composition were thus obtained:

|  | Calculated | Found |
|---|---|---|
| Phosphorus | 5.41% | 5.4% |
| Zinc | 5.67% | 5.0% |
| Sulfur | 11.16% | 10.9% |

EXAMPLE 12

Preparation of zinc-bis-0,0-[2,2-dimethyl-1,3-propanediyl-mono(p-trifluoromethylbenzoate)]-dithiophosphate of the formula:

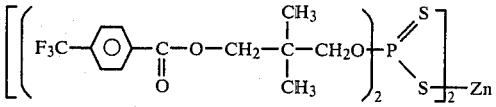

(a) Preparation of 2,2-dimethyl-1-propanol-mono(p-trifluoro-methylbenzoate)

The operation described in Example 1, part (a), was repeated, starting with:

190 g. (namely, 1 mol) of p-trifluoromethylbenzoic acid;
416 g. (namely, 4 mols) of neopentylglycol; and
14 g. of CLARCIL for 7 hours at 170° C.

269 g. of the desired ester were thus obtained in a purity of 90 percent and a yield of 87.7 percent.

(b) Preparation of bis-0,0-[2,2-dimethyl-1,3-propanediyl-mono(p-trifluoromethylbenzoate)]-dithiophosphoric acid The operation described in Example 1, part (b), was repeated, starting with:

184 g. (namely, 0.6 mol) of the above-prepared ester; and
33.5 g. (namely, 0.15 mol) of $P_2S_5$.

190 g. of the desired dithiophosphoric acid were obtained having the following composition:

|  | Calculated | Found |
|---|---|---|
| Phosphorus | 4.80% | 4.6% |
| Sulfur | 9.91% | 9.7% |

(c) Neutralization by zinc oxide

The operation described in Example 1, part (c), was repeated, starting with:

129 g. (namely, 0.2 mol) of the above-prepared dithiophosphoric acid; and
10.5 g. (namely, 0.13 mol) of ZnO (30 percent excess).

130 g. of the desired zinc dithiophosphate of a pH of 4.5 were thus obtained having the following composition:

|  | Calculated | Found |
|---|---|---|
| Phosphorus | 4.58% | 4.4% |
| Zinc | 4.80% | 4.4% |
| Sulfur | 9.45% | 9.2% |

EXAMPLE 13

Preparation of zinc-bis-0,0-[2,2-dimethyl-1,3-propanediyl-mono(9,10-dibromo-octadecanoate)]-dithiophosphate of the formula:

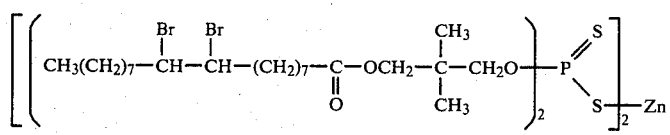

(a) Preparation of 2,2-dimethyl-1-propanol-mono(9,10-dibromooctadecanoate)

The operation described in Example 1, part (a), was repeated, starting with:

442 g. (namely, 1 mol) of 9,10-dibromo-octadecanoic acid;
416 g. (namely, 4 mols) of neopentylglycol; and
14 g. of CLARCIL
for 7 hours at 170° C.

428 g. of the desired ester of a purity of 89 percent were recovered in a yield of 72.1 percent.

(b) Preparation of bis-0,0-[2,2-dimethyl-1,3-propanediyl-mono(9,10-bromo-octadecanoate)]-dithiophosphoric acid The operation described in Example 1, part (b), was repeated, starting with:

360 g. (namely, 0.6 mol) of the above-prepared ester; and
33.5 g. (namely, 0.15 mol) of P2S5.

350 g. of the desired dithiophosphoric acid were obtained having the following composition:

|  | Calculated | Found |
| --- | --- | --- |
| Phosphorus | 2.70% | 2.6% |
| Sulfur | 5.57% | 5.4% |

(c) Neutralization by zinc oxide

The operation described in Example 1, part (c), was repeated, starting with:

237 g. (namely, 0.2 mol) of the above-prepared dithiophosphoric acid; and
10.5 g. (namely, 0.13 mol) of ZnO (30 percent excess).

200 g. of the desired zinc dithiophosphate of a pH of 5.1 were thus obtained having the following composition:

|  | Calculated | Found |
| --- | --- | --- |
| Phosphorus | 2.62% | 2.7% |
| Zinc | 2.75% | 2.5% |
| Sulfur | 5.41% | 5.3% |

EXAMPLE 14

Preparation of zinc-bis-0,0-[2,2-dimethyl-1,3-propanediyl-mono(11-bromo-undecanoate)]-dithiophosphate of the formula:

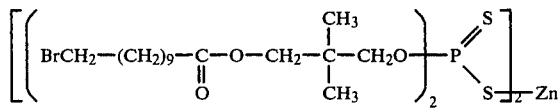

(a) Preparation of 2,2-dimethyl-1-propanol-mono(11-bromo-undecanoate)

The operation described in Example 1, part (a), was repeated, starting with:

265 g. (namely, 1 mol) of 11-bromo-undecanoic acid;
416 g. (namely, 4 mols) of neopentylglycol;
14 g. CLARCIL
for 4 hours at 170° C.

334 g. of the desired ester of a purity of 91 percent were recovered in a yield of 86.6 percent.

(b) Preparation of bis-0,0-[2,2-dimethyl-1,3-propanediyl-mono(11-bmomo-undecanoate)]-dithiophosphoric acid The operation described in Example 1, part (b), was repeated, starting with:

232 g. (namely, 0.6 mol) of the above-prepared ester; and
33.5 g. (namely, 0.15 mol) of P2S5.

220 g. of the desired dithiophosphoric acid were obtained having the following composition:

|  | Calculated | Found |
| --- | --- | --- |
| Phosphorus | 3.89% | 3.6% |
| Sulfur | 8.04% | 7.8% |

(c) Neutralization by zinc oxide

The operation described in Example 1, part (c), was repeated, starting with:

159 g. (namely, 0.2 mol) of the above-prepared dithiophosphoric acid; and
10.5 g. (namely, 0.13 mol) of ZnO (30 percent excess).

160 g. of the desired zinc dithiophosphate of a pH of 5.1 were thus obtained, having the following composition:

|  | Calculated | Found |
| --- | --- | --- |
| Phosphorus | 3.75% | 3.6% |
| Zinc | 3.93% | 3.2% |
| Sulfur | 7.73% | 7.8% |

EXAMPLE 15

Preparation of zinc-bis-0,0-[2,2-dimethyl-1,3-propanediyl-mono(2,3-dichloro-propanoate)]-dithiophosphate of the formula:

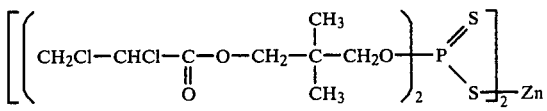

(a) Preparation of 2,2-dimethyl-1-propanol-mono(2,3-dichloro-propanoate)

The operation described in Example 1, part (a), was repeated, starting with:

143. g. (namely, 1 mol) of dichloropropanoic acid;
416 g. (namely, 4 mols) of neopentylglycol; and
14 g. of CLARCIL
for 5 hours at 140° C.

197 g. of the desired ester of a purity of 90 percent were recovered in a yield of 77.4 percent.

(b) Preparation of bis-0,0-[2,2-dimethyl-1,3-propanediyl-mono(2,3-dichloro-propanoate)]-dithiophosphoric acid The operation described in Example 1, part (b), was repeated, starting with:

153 g. (namely, 0.6 mol) of the above-prepared ester; and
33.5 g. (namely, 0.15 mol) of P2S5.

159 g. of the desired dithiophosphoric acid were obtained having the following composition:

|  | Calculated | Found |
| --- | --- | --- |
| Phosphorus | 5.62% | 5.6% |
| Sulfur | 11.59% | 11.65% |

(c) Neutralization by zinc oxide

The operation described in Example 1, part (c), was repeated, starting with:

110 g. (namely, 0.2 mol) of the above-prepared dithiophosphoric acid; and 10.5 g. (namely, 0.13 mol) of ZnO (30 percent excess).

108 g. of the desired zinc dithiophosphate of a pH of 5.0 were thus obtained having the following composition:

|  | Calculated | Found |
|---|---|---|
| Phosphorus | 5.31% | 5.2% |
| Zinc | 5.57% | 5.1% |
| Sulfur | 10.97% | 10.8% |

EXAMPLE 16

Preparation of zinc-bis-O,O-[2,2-dimethyl-1,3-propanediyl-mono(p-chlorobenzoate)]-dithiophosphate of the formula:

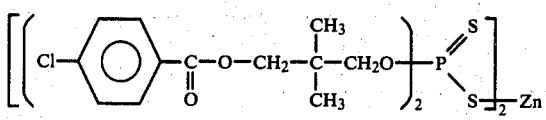

(a) Preparation of 2,2-dimethyl-1-propanol-mono(p-chloro-benzoate)

The operation described in Example 1, part (a), was repeated, starting with:

156.5 g. (namely, 1 mol) of p-chlorobenzoic acid;
416 g. (namely, 4 mols) of neopentylglycol; and
14 g. of CLARCIL
for 6 hours at 160° C.

190 g. of the desired ester were recovered in a yield of 76 percent with a purity of 97 percent.

(b) Preparation of bis-O,O-[2,2-dimethyl-1,3-propanediyl-mono(p-chlorobenzoate)]-dithiophosphoric acid The operation described in Example 1, part (b), was repeated, starting from:

150 g. (namely, 0.6 mol) of the above-prepared ester; and
33.5 g. (namely, 0.15 mol) of $P_2S_5$.

160 g. of the desired dithiophosphoric acid were obtained having the following composition:

|  | Calculated | Found |
|---|---|---|
| Phosphorus | 5.35% | 5.1% |
| Sulfur | 11.05% | 10.9% |

(c) Neutralization by zinc oxide

The operation described in Example 1, part (c), was repeated, starting with:

115.8 g. (namely, 0.2 mol) of the above-prepared dithiophosphoric acid; and
10.5 g. (namely, 0.13 mol) of ZnO (30 percent excess).

110 g. of the desired zinc dithiophosphate of a pH of 5.4 having the following composition were thus obtained:

|  | Calculated | Found |
|---|---|---|
| Phosphorus | 5.08% | 4.9% |
| Zinc | 5.32% | 5.1% |
| Sulfur | 10.48% | 9.8% |

EXAMPLE 17

Preparation of zinc-bis-O,O-(2,2-dimethyl-1,3-propanediylmononicotinate)-dithiophosphate of the formula:

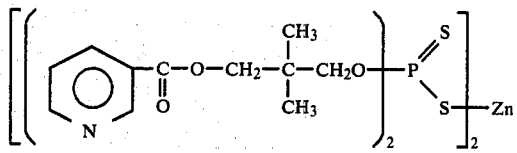

(a) Preparation of 2,2-dimethyl-1-propanol-mononicotinate

The operation described in Example 1, part (a), was repeated, starting with:

123 g. (namely, 1 mol) of nicotinic acid;
416 g. (namely, 4 mols) of neopentylglycol; and
14 g. of CLARCIL
for 6 hours at 190° C.

112 g. of the desired ester of a purity of 99 percent were recovered in a yield of 53 percent.

(b) Preparation of bis-O,O-(2,2-dimethyl-1,3-propanediyl-mononicotinate)-dithiophosphoric acid The operation described in Example 1, part (b), was repeated, starting with:

85 g. (namely, 0.4 mol) of the above-prepared ester; and
22.2 g. (namely, 0.1 mol) of $P_2S_5$.

98 g. of the desired dithiophosphoric acid were obtained, having the following composition:

|  | Calculated | Found |
|---|---|---|
| Phosphorus | 6.05% | 6.0% |
| Sulfur | 12.50% | 11.9% |

(c) Neutralization by zinc oxide

The operation described in Example 1, part (c), was repeated, starting with:

51.2 g. (namely, 0.1 mol) of the above-prepared dithiophosphoric acid; and
5.3 g. (namely, 0.065 mol) of ZnO (30 percent excess).

49 g. of the desired zinc dithiophosphate of a pH of 3.7 and the following composition were thus obtained:

|  | Calculated | Found |
|---|---|---|
| Phosphorus | 5.70% | 5.7% |
| Zinc | 5.98% | 5.7% |
| Sulfur | 11.78% | 10.7% |

EXAMPLE 18

Preparation of zinc-bis-O,O-(2,2-dimethyl-1,3-propanediyl monostearate)-dithiophosphate of the formula:

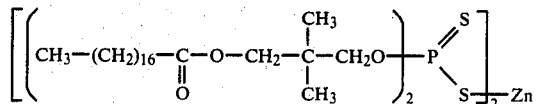

(a) Preparation of 2,2-dimethyl-1-propanolmonostearate

The operation described in Example 1, part (a), was repeated, starting with:

284 g. (namely, 1 mol) of stearic acid;
416 g. (namely, 4 mols) of neopentylglycol; and
14 g. of CLARCIL
for 3 hours at 130° C.

298 g. of the desired ester were recovered in a yield of 80.5 percent with a purity of 100 percent.

(b) Preparation of bis-O,O-(2,2-dimethyl-1,3-propanediyl-monostearate)-dithiophosphoric acid The operation described in Example 1, part (b), was repeated, starting with:

222 g. (namely, 0.6 mol) of the above-prepared ester; and
32.5 g. (namely, 0.15 mol) of $P_2S_5$.

240 g. of the desired dithiophosphoric acid were obtained having the following composition:

|  | Calculated | Found |
| --- | --- | --- |
| Phosphorus | 3.72% | 3.62% |
| Sulfur | 7.67% | 7.2% |

(c) Neutralization by zinc oxide

The operation described in Example 1, part (c), was repeated, starting with:

167 g. (namely, 0.2 mol) of the above-prepared dithiophosphoric acid; and
10.5 g. (namely, 0.13 mol) of ZnO (30 percent excess).

165 g. of the desired zinc dithiophosphate of a pH of 5.4 were obtained having the following composition:

|  | Calculated | Found |
| --- | --- | --- |
| Phosphorus | 3.58% | 3.3% |
| Zinc | 3.76% | 3.5% |
| Sulfur | 7.39% | 7.1% |

EXAMPLE 19

Preparation of zinc-bis-O,O-(2,2-dimethyl-1,3-propanediylmonoacetate)-dithiophosphate of the formula:

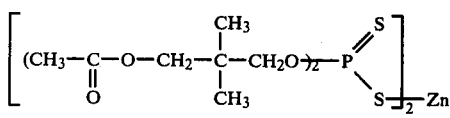

(a) Preparation of 2,2-dimethyl-1-propanol-monoacetate

The operation described in Example 1, part (a), was repeated, starting with:

60 g. (namely, 1 mol) of acetic acid;
416 g. (namely, 4 mols) of neopentylglycol; and
14 g. of CLARCIL
for 5 hours at 100° C.

59 g. of the desired ester of a purity of 80 percent were recovered, with a yield of 32 percent.

(b) Preparation of bis-O,O-(2,2-dimethyl-1,3-propanediyl-monoacetate)-dithiophosphoric acid The operation described in Example 1, part (b), was repeated, starting with:

55 g. (namely, 0.3 mol) of the above-prepared ester; and
16.7 g. (namely, 0.075 mol) of $P_2S_5$.

50 g. of the desired dithiophosphoric acid having the following composition were obtained:

|  | Calculated | Found |
| --- | --- | --- |
| Phosphorus | 8.03% | 8.5% |
| Sulfur | 16.58% | 16.5% |

(c) Neutralization by zinc oxide

The operation described in Example 1, part (c), was repeated, starting with:

38.6 g. (namely, 0.1 mol) of the above-prepared dithiophosphoric acid; and
5.3 g. (namely, 0.065 mol) of ZnO (30 percent excess).

40 g. of the desired zinc dithiophosphate of a pH of 3.5 were obtained having the following composition:

|  | Calculated | Found |
| --- | --- | --- |
| Phosphorus | 7.43% | 7.6% |
| Zinc | 7.78% | 6.8% |
| Sulfur | 15.33% | 14.0% |

EXAMPLE 20

Preparation of zinc-bis-O,O-(2,2-dimethyl-1,3-propanediylmonobenzoate)-dithiophosphate of the formula:

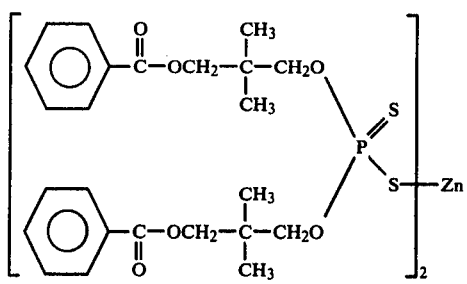

(a) Preparation of 2,2-dimethyl-1-propanol-monobenzoate

The operation described in Example 1, part (a), was repeated, starting with:

122 g. (namely, 1 mol) of benzoic acid;
416 g. (namely, 4 mols) of neopentylglycol; and
14 g. of CLARCIL
at for 7 hours at 170° C.

185 g. of the desired ester of a purity of 98 percent were recovered, with a yield of 87 percent.

(b) Preparation of bis-O,O-(2,2-dimethyl-1,3-propanediyl-monobenzoate)-dithiophosphoric acid The operation described in Example 1, part (b), was repeated, starting with:

104 g. (namely, 0.5 mol) of the above-prepared ester; and
27.8 g. (namely, 0.125 mol) of $P_2S_5$.

120 g. were obtained of dithiophosphoric acid having the formula:

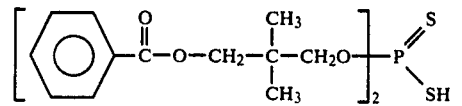

the composition of which was as follows:

| | Calculated | Found |
|---|---|---|
| Phosphorus | 6.08% | 6.21% |
| Sulfur | 12.55% | 11.21% |

(c) Neutralization by zinc oxide

The operation described in Example 1, part (c), was repeated, starting from:

102 g. (namely, 0.2 mol) of the above-prepared dithiophosphoric acid; and 10.5 g. (namely, 0.13 mol) of ZnO (30 percent excess).

105 g. of the desired zinc dithiophosphate of a pH of 3.5 were thus obtained, the composition of which was as follows:

| | Calculated | Found |
|---|---|---|
| Phosphorus | 5.77% | 5.6% |
| Zinc | 6.05% | 6.5% |
| Sulfur | 11.91% | 11.3% |

EXAMPLE 21

Preparation of zinc-bis-O,O-[2,2-dimethyl-1,3-propanediylmono(cyclohexane-carboxylate)]-dithiophosphate of the formula:

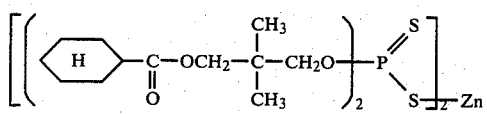

(a) Preparation of 2,2-dimethyl-1-propanol-mono(cyclohexanoate)

The operation described in Example 1, part (a), was repeated, starting with:

128 g. (namely, 1 mol) of cyclohexane-carboxylic acid;

416 g. (namely, 4 mols) of neopentylglycol; and 14 g. of CLARCIL for 6½ hours at 160° C.

105 g. of the desired ester were obtained in a purity of 84 percent with a yield of 41.2 percent.

(b) Preparation of bis-O,O-(2,2-dimethyl-1,3-propanediyl-monocyclohexanoate)-dithiophosphoric acid The operation described in Example 1, part (b), was repeated, starting with:

85.5 g. (namely, 0.4 mol) of the above-prepared ester; and 22.2 g. (namely, 0.1 mol) of $P_2S_5$.

There were obtained 100 g. of the desired dithiophosphoric acid having the following composition:

| | Calculated | Found |
|---|---|---|
| Phosphorus | 5.94% | 6.1% |
| Sulfur | 12.26% | 12.8% |

(c) Neutralization by zinc oxide

The operation described in Example 1, part (c), was repeated, starting with:

78.3 g. (namely, 0.15 mol) of the above-prepared dithiophosphoric acid; and 7.9 g. (namely, 0.0925 mol) of ZnO (30 percent excess).

70 g. of the desired zinc dithiophosphate of a pH of 3.6 and the following composition were thus obtained:

| | Calculated | Found |
|---|---|---|
| Phosphorus | 5.60% | 5.55% |
| Zinc | 5.87% | 6.5% |
| Sulfur | 11.56% | 11.0% |

EXAMPLE 22

Preparation of zinc-bis-O,O-(2,2-dimethyl-1,3-propanediylmonomethacrylate)-dithiophosphate of the formula:

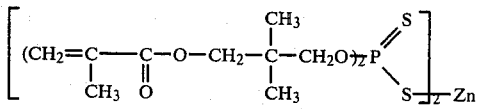

(a) Preparation of 2,2-dimethyl-1-propanolmonomethacrylate

The operation described in Example 1, part (a), was repeated, starting with:

86 g. (namely, 1 mol) of methacrylic acid;

416 g. (namely, 4 mols) of neopentylglycol; and 14 g. of CLARCIL for 13 hours at 160° C.

82 g. of the desired ester in a purity of 83 percent were recovered with a yield of 40 percent.

(b) Preparation of bis-O,O-(2,2-dimethyl-1,3-propanediyl-monomethacrylate)-dithiophosphoric acid The operation described in Example 1, part (b), was repeated, starting with:

62 g. (namely, 0.3 mol) of the above-prepared ester; and 16.7 g. (namely, 0.075 mol) of $P_2S_5$.

60 g. of the desired dithiophosphoric acid having the following composition were obtained:

| | Calculated | Found |
|---|---|---|
| Phosphorus | 7.08% | 7.0% |
| Sulfur | 14.61% | 14.1% |

(c) Neutralization by zinc oxide

The operation described in Example 1, part (c), was repeated, starting with:

44 g. (namely, 0.1 mol) of the above-prepared dithiophosphoric acid;

5.3 g. (namely, 0.065 mol) of ZnO (30 percent excess).

40 g. of the desired zinc dithiophosphate of a pH of 4.9 and having the following composition were thus obtained:

| | Calculated | Found |
|---|---|---|
| Phosphorus | 6.60% | 6.5% |
| Zinc | 6.92% | 6.7% |
| Sulfur | 13.63% | 12.5% |

EXAMPLE 23

Preparation of zinc-bis-O,O-(2-ethyl-2-n-butyl-1,3-propanediyl-monooleate)-dithiophosphate of the formula:

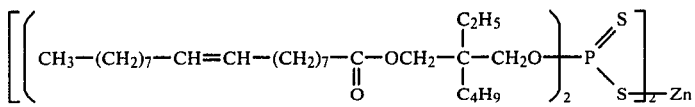

(a) Preparation of 2-ethyl-2-n-butyl-1-propanol-monooleate

The operation described in Example 1, part (a), was repeated, starting with:

282 g. (namely, 1 mol) of oleic acid;
640 g. (namely, 4 mols) of 2-ethyl-2-n-butyl-1,3-propanediyl; and
14 g. of CLARCIL for 4 hours at 170° C.

402 g. of the desired ester having a purity of 96 percent were thus recovered, with a yield of 91 percent.

(b) Preparation of bis-O,O-(2-ethyl-2-n-butyl-1,3-propanediyl-monooleate)-dithiophosphoric acid The operation described in Example 1, part (b), was repeated, starting with:

265 g. (namely, 0.6 mol) of the above-prepared ester; and
33.5 g. (namely, 0.15 mol) of P$_2$S$_5$.

280 g. of the desired dithiophosphoric acid having the following composition were obtained:

|  | Calculated | Found |
|---|---|---|
| Phosphorus | 3.29% | 3.40% |
| Sulfur | 6.79% | 6.80% |

(c) Neutralization by zinc oxide

The operation described in Example 1, part (c), was repeated, starting with:

188.5 g. (namely, 0.2 mol) of the above-prepared dithiophosphoric acid; and
10.5 g. (namely, 0.13 mol) of ZnO (30 percent excess).

180 g. of the desired zinc dithiophosphate of a pH of 5.8 and the following composition were thus obtained:

|  | Calculated | Found |
|---|---|---|
| Phosphorus | 3.18% | 3.2% |
| Zinc | 3.34% | 3.2% |
| Sulfur | 6.57% | 6.6% |

EXAMPLE 24

Preparation of zinc-bis-O,O-(2,2-dimethyl-1,3-propanediylmonoundecylenate)-dithiophosphate of the formula:

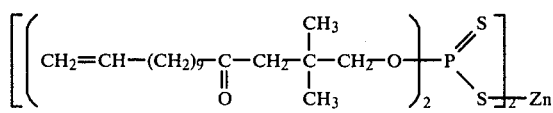

(a) Preparation of 2,2-dimethyl-propanediolmonoundecylenate

The operation described in Example 1, part (a), was repeated, starting with:

184 g. (namely, 1 mol) of undecylenic acid;
416 g. (namely, 4 mols) of neopentylglycol; and
14 g. of CLARCIL for 5 hours at 150° C.

248 g. of the desired ester having a purity of 98 percent were recovered, with a yield of 90 percent.

(b) Preparation of bis-O,O-(2,2-dimethyl-1,3-propanediyl-monoundecylenate)-dithiophosphoric acid The operation described in Example 1, part (b), was repeated, starting with:

165 g. (namely, 0.6 mol) of the above-prepared ester; and
33.5 g. (namely, 0.15 mol) of P$_2$S$_5$.

180 g. of the desired dithiophosphoric acid having the following composition were thus obtained:

|  | Calculated | Found |
|---|---|---|
| Phosphorus | 4.89% | 4.7% |
| Sulfur | 10.09% | 9.9% |

(c) Neutralization by zinc oxide

The operation described in Example 1, part (c), was repeated, starting with:

127 g. (namely, 0.2 mol) of the above-prepared dithiophosphoric acid; and
10.5 g. (namely, 0.13 mol) of ZnO (30 percent excess).

115 g. of the desired zinc dithiophosphate of a pH of 5.1 having the following composition were thus obtained:

|  | Calculated | Found |
|---|---|---|
| Phosphorus | 4.66% | 4.5% |
| Zinc | 4.88% | 4.7% |
| Sulfur | 9.26% | 9.5% |

EXAMPLE 25

A series of lubricating compositions were prepared by adding to a 10 W 30 oil in each case an amount of the additive product obtained in each of Examples 1 to 24, inclusive, which corresponds to 0.1 percent phosphorus.

The mechanical properties of this composition were tested on:

(1) a 4-ball machine, in accordance with ASTM Standard D 2783-69 T; this test gives the diameter in mm. of the imprint under a seizure load of 70, 90, 110 and 130 kg., as well as the welding load in kg.

(2) a Falex machine; this test gives the wear of the pin (that is to say, of the wear test piece) in mg. at the end of 30 minutes under a pressure of 500 pounds (271.5 kg.).

The resistance to oxidation of these compositions was evaluated by the Mobil oxidation test which consists in oxidizing 33 g. of oil containing the additive, heating it to 180° C. for 50 hours in the presence of oxidation catalysts (Pb-Cu), under a flow of air of 14 liters per hour, and measuring the increase in viscosity at 210° F. (98.9° C.) of the oxidized oil as compared with the new oil.

Comparable tests were carried out on compositions in which the additive product of Examples 1 to 24 was replaced by the same amount, expressed in % of phosphorus, of one of the following commercial additives, all containing phosphorus:

Additive A: "Eca 5215" marketed by Exxon
Additive B: "Lubrizol 797" marketed by Lubrizol
Additive C: "Improvex 33" marketed by Rhone-Poulenc
Additive D: "Oloa 260" marketed by Oronite
Additive E: "Oloa 269" marketed by Oronite The results of all of these tests are set forth in Tables I, I', and II, below.

It is noted that the additive compositions of the invention have a very good general level of performance with respect to their mechanical properties and have good constancy of these performances despite the oxidation. The anti-oxidant properties are also very good.

EXAMPLE 26

Lubricating compositions were prepared by adding to a 10 W 30 oil the additive product prepared in Example 1 in different concentrations, and they were compared with those obtained by the addition of Additives D and E in different concentrations. These compositions are tested in accordance with the methods described in the preceding example.

The results of these tests appear in Table III, below.

It is noted that the compositions obtained by means of the additives of Example 1 have a very good general level of performance, even with a low concentration of additive.

EXAMPLE 27

A lubricating composition was prepared by adding to a 10 W 30 oil an amount of product obtained in Example 1 which corresponds to 0.1 percent phosphorus.

Lubricating compositions were also prepared by addition of 0.1 percent phosphorus of Additives D, B, and E.

These compositions were tested as to their termal stability by the Cincinnati/Milacron Test; this test consists in maintaining the compositions at 135° C. for 138 hours in the presence of iron and copper and then measuring the following parameters:

(a) change in weight of the iron and copper specimens;
(b) weight of sediment;
(c) color of the copper test-piece (ASTM Test D-130);
(d) increase in viscosity.

The results of this test appear in Table IV, below. It is noted that the composition obtained employing the additive product of Example 1 shows very good thermal stability as compared with the commercial products, without corrosion of the iron or copper.

As will be apparent to those skilled in the lubricant additive art from the foregoing disclosure, in each of Examples 1 through 24, inclusive, the zinc oxide employed can be replaced by an equivalent amount of an oxide or other basic compound of a metal from Groups IIB, IIIB, IVB, and VIII of the Periodic System of the Elements. Among such metal compounds are the oxides of cadmium from group IIB, aluminium from Group IIIB, tin and lead from Group IVB, and iron, and cobalt, from Group VIII.

As employed throughout the present specification and the appended claims, the "Periodic System of the Elements" is intended to refer to that published by the Societe Chimique de France. Included among the metals of Group IIB are Zn, Cd, and Hg. Among the metals of Group IIIB are B, Al, Ga, In, and Tl. Among the metals of Group IVB are Si, Ge, Sn, and Pb. Group VIII includes Fe, Co, and Ni.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

TABLE I

| | | Mechanical Properties | | | | | | | |
|---|---|---|---|---|---|---|---|---|---|
| | | Before Oxidation | | | | | | After Oxidation | Oxidation Increase |
| Product of Example | % by Weight of Product | Seizing - imprint in mm. | | | | Welding Load in kg. | Falex in mg. | Seizing-imprint in mm. - 100 kg. | in Viscosity in % |
| | | 70 kg. | 90 kg. | 110 kg. | 130 kg. | | | | |
| | 2.78 | 0.4 | 0.8 | 2.5 | | 300 | 6.2 | 1.6 | 20 |
| 2 | 1.96 | 0.7 | 2.2 | — | | 300 | 7.1 | 1.7 | 40 |
| 3 | 1.45 | 1.7 | 2.6 | — | | 200 | 3.5 | — | gel |
| 4 | 1.53 | 0.9 | 2.7 | — | | 250 | 4.5 | 1.8 | 200 |
| 5 | 1.89 | 0.5 | 2.0 | 2.6 | | 300 | 6.0 | 1.5 | 30 |
| 6 | 1.75 | 1.2 | 2.3 | — | | 300 | 9.7 | 1.5 | 60 |
| 7 | 2.94 | 0.4 | 1.5 | 2.5 | | 300 | 5.1 | 1.6 | 30 |
| 8 | 1.96 | 1.0 | 1.9 | 2.7 | | 300 | 5.7 | 1.7 | 40 |
| 9 | 2.44 | 0.4 | 0.7 | 2.4 | | 300 | 6.1 | 1.3 | 40 |
| 10 | 1.92 | 0.8 | 1.7 | 2.6 | | 300 | 7.1 | 1.7 | 70 |
| 11 | 1.85 | 1.6 | 2.5 | — | | 250 | 8.0 | 1.8 | 100 |
| 12 | 2.27 | 0.5 | 1.6 | 2.6 | | 300 | 5.4 | 1.4 | 40 |
| 13 | 3.70 | 0.5 | 0.8 | 2.4 | | 300 | 3.9 | 1.2 | 30 |
| 14 | 2.78 | 0.6 | 0.9 | 2.6 | | 300 | 4.2 | 1.3 | 40 |
| 15 | 1.92 | 1.4 | 2.7 | — | | 250 | 10.5 | 1.8 | 100 |
| 16 | 2.04 | 1.8 | 2.5 | — | | 300 | 7.0 | 1.5 | 70 |
| 17 | 1.75 | 0.4 | 1.8 | 2.2 | | 300 | 7.2 | 1.9 | 200 |

TABLE I

| Product of Example | % by Weight of Product | Mechanical Properties | | | | | | After Oxidation Seizing imprint in mm. - 100 kg. | Oxidation Increase in Viscosity in % |
|---|---|---|---|---|---|---|---|---|---|
| | | Before Oxidation | | | | Welding Load in kg. | Falex in mg. | | |
| | | Seizing - imprint in mm. | | | | | | | |
| | | 70 kg. | 90 kg. | 110 kg. | 130 kg. | | | | |
| 18 | 3.03 | 0.5 | 0.9 | 2.4 | — | 300 | 5.4 | 1.5 | 40 |
| 19 | 1.32 | 2.2 | 2.7 | — | — | 200 | 2.5 | — | gel |
| 20 | 1.79 | 2.0 | 2.2 | — | — | 250 | 7.3 | 1.6 | 100 |
| 21 | 1.80 | 0.4 | 2.0 | 2.6 | — | 300 | 3.8 | 1.5 | 0 |
| 22 | 1.54 | 1.7 | 2.4 | — | — | 200 | 4.3 | — | gel |
| 23 | 3.12 | 0.9 | 2.0 | 2.5 | — | 300 | 9.5 | 1.5 | 40 |
| 24 | 2.22 | 0.6 | 0.9 | 2.6 | — | 300 | 6.4 | 1.6 | 30 |

TABLE II

| Product | % by Weight of Product | Mechanical Properties | | | | | | After Oxidation Seizing - imprint in mm. - 100 kg. | Oxidation Increase in Viscosity in % |
|---|---|---|---|---|---|---|---|---|---|
| | | Before Oxidation | | | | Welding Load in kg. | Falex in mg. | | |
| | | Seizing - imprint in mm. | | | | | | | |
| | | 70 kg. | 90 kg. | 110 kg. | 130 kg. | | | | |
| A | 3.73 | — | 0.5 | 0.5 | 2.5 | 300 | 8.7 | 2.0 | 80 |
| B | 4.08 | — | 2.6 | — | — | 200 | 1.0 | — | gel |
| C | 1.24 | — | 2.5 | — | — | 250 | 14.9 | — | gel |
| D | 3.45 | — | 2.6 | — | — | 300 | 23.0 | 2.4 | 90 |
| E | 1.35 | — | 0.5 | 2.2 | — | 250 | 10.5 | 2.6 | 150 |

TABLE III

| Product | % by Weight of Product | Before Oxidation | | | | Welding Load in kg. | Falex in mg. | After Oxidation Seizing imprint in mm. - 100 kg. | Oxidation Increase in Viscosity in % |
|---|---|---|---|---|---|---|---|---|---|
| | | Seizing - imprint in mm. | | | | | | | |
| | | 70 kg. | 90 kg. | 110 kg. | 130 kg. | | | | |
| Ex. 1 | 0.1 | 2.3 | 3 | — | — | 200 | — | — | gel |
| — | 0.5 | 2.4 | 2.4 | — | — | 250 | 12 | 2.6 | 150 |
| — | 2.78 | 0.4 | 0.8 | 2.5 | — | 300 | 6.2 | 1.6 | 20 |
| — | 4.5 | 0.3 | 0.6 | 2.1 | — | 300 | 4.6 | 1.4 | 15 |
| E | 0.1 | 0.7 | 2.4 | — | — | 200 | — | — | gel |
| | 1 | 0.6 | 0.8 | 2.6 | — | 200 | 20.0 | — | gel |
| | 1.35 | | 0.42 | 2.2 | — | 250 | 10.5 | 2.6 | 150 |
| | 3 | | 0.4 | 2.0 | — | 250 | 10.1 | 2.5 | 90 |
| | 4.5 | | 0.3 | 2.0 | — | 250 | 9.9 | 2.5 | 50 |
| D | 0.1 | 2.4 | — | — | — | 200 | — | — | gel |
| | 1.5 | 2.0 | 2.2 | — | — | | 24.1 | 1.8 | 150 |
| | 3.45 | 2.0 | 2.6 | — | — | 300 | 22.1 | 2.4 | 90 |
| | 4.5 | 0.6 | 2.8 | — | — | 300 | 23.2 | 2.4 | 50 |

TABLE IV

| Product | Fe Test Piece | Cu Test Piece | Weight of Sediment mg. | Increase in Viscosity in % | Appearance | Copper Blade ASTM D 130 |
|---|---|---|---|---|---|---|
| Ex. 1 | +0.4 mg. | 30 0.3 mg. | 0 | 10 | clear | 2 C |
| D | +0.8 mg. | −23.7 mg. | 21 | 50 | cloudy | 4 a |
| B | −1 mg. | −66.7 mg. | 10 | 30 | cloudy | 4 a |
| E | +0.4 mg. | −20.3 mg. | 31 | 15 | clear | 4 b |

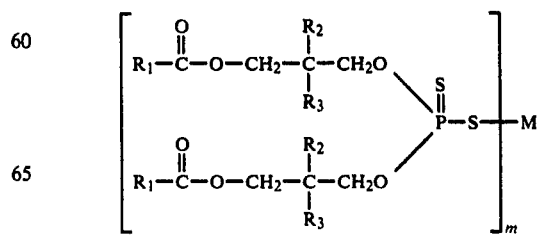

What is claimed is:

1. A metallic dithiophosphate having the formula:

in which:

R₁ represents:
(a) a linear or branched alkyl radical containing from about 1 to 24 carbon atoms;
(b) a linear or branched alkenyl radical containing from about 2 to 24 carbon atoms;
(c) a saturated or unsaturated cycloaliphatic or polycycloaliphatic radical containing from about 3 to 20 carbon atoms;
(d) an aryl radical containing from 6 to 14 carbon atoms;
(e) a heterocyclic radical containing one or more heteroelements selected from among nitrogen, sulfur and oxygen;

R₂ and R₃ are alkyl radicals containing from about 1 to 12 carbon atoms;

m represents the valence of the metal M;

M represents a metal of groups IIB, IIIB, IVB, or VIII of the Periodic System of the Elements.

2. A metallic dithiophosphate according to claim 1, wherein the alkyl radical is substituted by at least one member selected from the class consisting of phenyl, halo, and heterocyclic groups containing at least one heterocyclic element selected from the class consisting of nitrogen, sulfur, and oxygen.

3. A metallic dithiophosphate according to claim 1, wherein the alkenyl radical is substituted by at least one member selected from the class consisting of phenyl, halo, and heterocyclic groups containing at least one heterocyclic element selected from the class consisting of nitrogen, sulfur, and oxygen.

4. A metallic dithiophosphate according to claim 1, wherein the cycloaliphatic or polycycloaliphatic radical is substituted by at least one alkyl group containing from about 1 to 12 carbon atoms or a halogen atom.

5. A metallic dithiophosphate according to claim 1, wherein the aryl radical is substituted by at least one alkyl group containing from about 1 to 12 carbon atoms, or a halogen, or halo alkyl group.

6. A metallic dithiophosphate according to claim 1, wherein the heterocyclic radical is substituted by at least one alkyl group containing from about 1 to 12 carbon atoms or a halogen atom.

7. A metallic dithiophosphate according to claim 1, wherein the metal M is zinc.

8. A metallic dithiophosphate according to claim 1, wherein R₁ contains from about 1 to 17 carbon atoms when it represents an alkyl radical, from about 2 to 17 carbon atoms when it represents an alkenyl radical, and 6 carbon atoms when it represents an aryl radical.

9. A metallic dithiophosphate according to claim 1, wherein R₂ and R₃ contain from about 1 to 4 carbon atoms.

10. A metallic dithiophosphate according to claim 9, wherein R₂ and R₃ represent a member selected from the class consisting of methyl, ethyl, and butyl radicals.

11. A metallic dithiophosphate according to claim 1, wherein R₁ represents one of the following radicals: methyl, 1,2-dichloro-ethyl, heptyl, 10-bromo-decyl, 8,9-dibromo-hepta-decyl, heptadecyl, vinyl, phenylvinylene, 2-furyl-vinylene, isopropenyl, decenyl, heptadecenyl, cyclopropyl, cyclohexyl, cyclohexenyl, C₁₉H₂₉ derived from abietic acid, phenyl, p-chlorophenyl, p-trifluoromethylphenyl, 2,3-dimethyl-1-phenyl, p-octylphenyl, 2-furyl-4-methyl-5-thiazolyl, and 3-pyridyl.

12. A method of preparing a metallic dithiophosphate according to claim 1, comprising reacting a monoester alcohol of the formula:

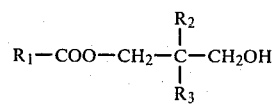

with an amount of P₂S₅ in excess of about 5 to 20 mol percent referred to the amount of P₂S₅ stoichiometrically necessary in order to obtain a dithiophosphoric acid of the formula:

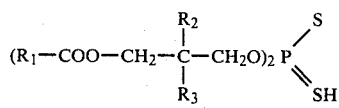

and reacting the resultant dithiophosphoric acid with an amount of basic compound of metal M which is between the amount stoichiometrically necessary to neutralize the dithiophosphoric acid and twice said stoichiometric amount.

13. A method according to claim 12, wherein the basic compound of metal M is zinc oxide.

14. A method according to claim 12, wherein the dithiophosphoric acid is prepared at a temperature of between about 50° and 200° C. with an amount of P₂S₅ corresponding to a 5 percent molar excess referred to the stoichiometric amount and the dithiophosphoric acid is neutralized by the basic compound of metal M at a temperature between about 20° and 200° C. with an amount of basic compound of metal M which is between about 1.1 times and 1.5 times the stoichiometric amount.

15. A method according to claim 14, wherein the dithiophosphoric acid is prepared at a temperature between about 70° and 150° C. and is neutralized at a temperature between about 60° and 150° C.

16. A method according to any of Claims 12 to 15, wherein the monoester alcohols employed are those derived from alcohols selected from among neopentylglycol and 2-ethyl-2-n-butyl-1,3-propanediol and acids selected from among acetic acid, 2,3-dichloropropanoic acid, octanoic acid, 11-bromo-undecanoic acid, 9,10-dibromooctadecanoic acid, stearic acid, acrylic acid, cinnamic acid, 2-furanacrylic acid, methacrylic acid, undecylenic acid, oleic acid, cyclopropane-carboxylic acid, 1-cyclohexene carboxylic acid, cyclohexane-carboxylic acid, abietic acid, benzoic acid, p-chlorobenzoic acid, p-trifluoromethylbenzoic acid, 2,3-dimethylbenzoic acid, p-n-octyl-benzoic acid, 2-furan-carboxylic acid, 4-methylthiazol-5-carboxylic acid, and acid.

17. A lubricating composition comprising a major proportion of at least one lubricating oil and between about 0.2 and 10 percent by weight of a metallic dithiophosphate according to claim 1.

18. A lubricating composition comprising a major proportion of at least one lubricating oil and between about 0.2 and 10 percent by weight of a metallic dithiophosphate according to claim 7.

19. A lubricating composition comprising a major proportion of at least one lubricating oil and between about 0.2 and 10 percent by weight of a metallic dithiophosphate according to claim 11.

20. A metallic dithiophosphate having the formula:

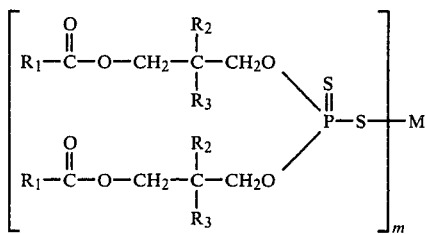

in which:

R₁ represents:
- (a) a linear or branched alkyl radical containing from about 1 to 24 carbon atoms;
- (b) a linear or branched alkenyl radical containing from about 2 to 24 carbon atoms;
- (c) a saturated or unsaturated cycloaliphatic or polycycloaliphatic radical containing from about 3 to 20 carbon atoms; or
- (d) an aryl radical containing from 6 to 14 carbon atoms;

$R_2$ and $R_3$ are alkyl radicals containing from about 1 to 12 carbon atoms;

m represents the valence of the metal M; and

M represents a metal of groups IIB, IIIB, IVB, or VIII of the Periodic System of the Elements.

21. A metallic dithiophosphate according to claim 20, wherein the alkyl radical is substituted by at least one member selected from the class consisting of phenyl and halo.

22. A metallic dithiophosphate according to claim 20, wherein the alkenyl radical is substituted by at least one member selected from the class consisting of phenyl and halo.

23. A metallic dithiophosphate according to claim 20, wherein the cycloaliphatic or polycycloaliphatic radical is substituted by at least one alkyl group containing from about 1 to 12 carbon atoms or a halogen atom.

24. A metallic dithiophosphate according to claim 20, wherein the aryl radical is substituted by at least one alkyl group containing from about 1 to 12 carbon atoms, or a halogen, or halo alkyl group.

25. A metallic dithiophosphate according to claim 20, wherein the metal M is zinc.

26. A metallic dithiophosphate according to claim 20, wherein $R_1$ contains from about 1 to 17 carbon atoms when it represents an alkyl radical, from about 2 to 17 carbon atoms when it represents an alkenyl radical, and 6 carbon atoms when it represents an aryl radical.

27. A metallic dithiophosphate according to claim 20, wherein $R_2$ and $R_3$ contain from about 1 to 4 carbon atoms.

28. A metallic dithiophosphate according to claim 27, wherein $R_2$ and $R_3$ represent a member selected from the class consisting of methyl, ethyl, and butyl radicals.

29. A metallic dithiophosphate according to claim 1, wherein $R_1$ represents one of the following radicals: methyl, 1,2-dichloro-ethyl, heptyl, 10-bromo-decyl, 8,9-dibromo-heptadecyl, heptadecyl, vinyl, phenylvinylene, isopropenyl, decenyl, heptadecenyl, cyclopropyl, cyclohexyl, cyclohexenyl, $C_{19}H_{29}$ derived from abietic acid, phenyl, p-chlorophenyl, p-trifluoromethylphenyl, 2,3-dimethyl-1-phenyl, and p-octylphenyl.

30. A method of preparing a metallic dithiophosphate according to claim 20, comprising reacting a monoester alcohol of the formula:

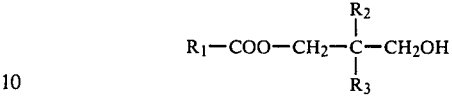

with an amount of $P_2S_5$ in excess of about 5 to 20 mol percent referred to the amount of $P_2S_5$ stoichiometrically necessary in order to obtain a dithiophosphoric acid of the formula:

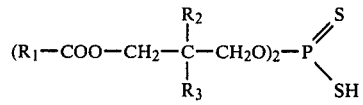

and reacting the resultant dithiophosphoric acid with an amount of basic compound of metal M which is between the amount stoichiometrically necessary to neutralize the dithiophosphoric acid and twice said stoichiometric amount.

31. A method according to claim 30, wherein the basic compound of metal M is zinc oxide.

32. A method according to claim 30, wherein the dithiophosphoric acid is prepared at a temperature of between about 50° and 200° C. with an amount of $P_2S_5$ corresponding to a 5 percent molar excess referred to the stoichiometric amount and the dithiophosphoric acid is neutralized by the basic compound of metal M at a temperature between about 20° and 200° C. with an amount of basic compound of metal M which is between about 1.1 times and 1.5 times the stoichiometric amount.

33. A method according to claim 32, wherein the dithiophosphoric acid is prepared at a temperature between about 70° and 150° C. and is neutralized at a temperature between about 60° and 150° C.

34. A method according to any of claims 30 to 33, wherein the monoester alcohols employed are those derived from alcohols selected from among neopentylglycol and 2-ethyl-2-n-butyl-1,3-propanediol and acids selected from among acetic acid, 2,3-dichloropropanoic acid, octanoic acid, 11-bromoundecanoic acid, 9,10-dibromo-octadecanoic acid, stearic acid, acrylic acid, cinnamic acid, methacrylic acid, undecylenic acid, oleic acid, cyclopropane-carboxylic acid, 1-cyclohexene carboxylic acid, cyclohexane-carboxylic acid, abietic acid, benzoic acid, p-chlorobenzoic acid, p-tri-fluoromethylbenzoic acid, 2,3-dimethylbenzoic acid, and p-n-octyl-benzoic acid.

35. A lubricating composition comprising a major proportion of at least one lubricating oil and between about 0.2 and 10 percent by weight of a metallic dithiophosphate according to claim 20.

36. A lubricating composition comprising a major proportion of at least one lubricating oil and between about 0.2 and 10 percent by weight of a metallic dithiophosphate according to claim 25.

37. A lubricating composition comprising a major proportion of at least one lubricating oil and between about 0.2 and 10 percent by weight of a metallic dithiophosphate according to claim 29.

* * * * *

UNITED STATES PATENT AND TRADEMARK OFFICE
CERTIFICATE OF CORRECTION

PATENT NO. : 4,288,335
DATED : September 8, 1981
INVENTOR(S) : Georges Rivier

It is certified that error appears in the above—identified patent and that said Letters Patent is hereby corrected as shown below:

Column 15, line 63, "bmomo" should be -- bromo -- ;

Column 20, line 50, delete "at" first occurrence.

Column 24, line 39, "9.26%" should be -- 9.62% -- ;

Column 25, Table I, under "Example" insert -- 1 -- ;

Column 27, line 1, "TABLE I" should be -- TABLE I' -- ;

Table III, bridging columns 27 and 28, insert the following below the second line of entries as the third line of entries:

-- -  1.5  2  2  -  -  300  9.5  2  30  -- ; and

Column 30, line 56, insert -- nicotinic -- after "and".

Signed and Sealed this

Twentieth Day of April 1982

[SEAL]

Attest:

GERALD J. MOSSINGHOFF

Attesting Officer    Commissioner of Patents and Trademarks